(12) United States Patent
Hampton

(10) Patent No.: US 7,065,396 B2
(45) Date of Patent: Jun. 20, 2006

(54) SYSTEM AND METHOD FOR NON-INVASIVE MONITORING OF PHYSIOLOGICAL PARAMETERS

(75) Inventor: Thomas G. Hampton, Framingham, MA (US)

(73) Assignee: The Curavita Corporation, Boston, MA (US)

( * ) Notice: Subject to any disclaimer, the term of this patent is extended or adjusted under 35 U.S.C. 154(b) by 601 days.

(21) Appl. No.: 10/209,103

(22) Filed: Jul. 30, 2002

(65) Prior Publication Data

US 2003/0028117 A1 Feb. 6, 2003

Related U.S. Application Data

(60) Provisional application No. 60/309,008, filed on Jul. 30, 2001.

(51) Int. Cl.
*A61B 5/04* (2006.01)

(52) U.S. Cl. ........................ 600/509; 600/393; 600/384

(58) Field of Classification Search ................ 600/372, 600/382, 384, 386, 393, 509, 523, 547, 559, 600/301, 306; 128/899
See application file for complete search history.

(56) References Cited

U.S. PATENT DOCUMENTS

| | | | |
|---|---|---|---|
| 3,170,459 A * | 2/1965 | Phipps et al. ................ 600/391 |
| 3,628,525 A | 12/1971 | Polanyi et al. | |
| 3,709,212 A * | 1/1973 | Koeblitz ..................... 600/508 |
| 4,030,485 A | 6/1977 | Warner | |
| 4,278,095 A | 7/1981 | Lapeyre | |
| 4,323,852 A * | 4/1982 | Walker ........................... 330/9 |
| 4,703,758 A | 11/1987 | Omura | |
| 4,907,596 A | 3/1990 | Schmid et al. | |
| 4,913,150 A | 4/1990 | Cheung et al. | |
| 5,054,493 A | 10/1991 | Cohn et al. | |
| 5,237,997 A | 8/1993 | Greubel et al. | |
| 6,224,549 B1 * | 5/2001 | Drongelen ................... 600/300 |

OTHER PUBLICATIONS

King, R.L., et al. "The electrocardiogram of a Beluga whale." *Circulation*. Sep. 1953; 8(3):387-93.

* cited by examiner

*Primary Examiner*—Robert E Pezzuto
*Assistant Examiner*—Brian T Gedeon
(74) *Attorney, Agent, or Firm*—Lahive & Cockfield, LLP

(57) ABSTRACT

A method and apparatus for enabling the non-invasive acquisition of physiological parameters of a mammal, while allowing the mammal to move around a predetermined area is provided. In accordance with one example embodiment, a monitoring device for non-invasively acquiring physiological measurements of a mammal is provided. The device includes a first electrode configured to attach to an ear of the mammal in a manner suitable for obtaining a first electrical signal. A second electrode is configured to attach to a first alternate location of the mammal in a manner suitable for obtaining a second electrical signal. A third electrode is configured to attach to a second alternate location of the mammal in a manner suitable for obtaining a third electrical signal. The first electrode, second electrode, and third electrode are in communication with a signal receiver. Physiological parameters, such as those associated with electrocardiograms, can be obtained using the monitoring device.

6 Claims, 7 Drawing Sheets

SYSTEM AND METHOD FOR NON-INVASIVE MONITORING OF PHYSIOLOGICAL PARAMETERS

RELATED APPLICATION

This application claims priority to, and the benefit of, U.S. Provisional Application No. 60/309,008, filed Jul. 30, 2001, for all subject matter common to the Provisional Application and this Application. The disclosure of said Provisional Application is hereby incorporated herein by reference in its entirety.

FIELD OF THE INVENTION

The present invention relates to a system and method of non-invasively acquiring physiological parameters, and more particularly to a system for monitoring physiological parameters, electrical signals for creating electrocardiograms, in mammals, while allowing relatively free movement of the mammal.

BACKGROUND OF THE INVENTION

Animals, for example mice, are used extensively in the examination of gene function, the development of drugs, and in other laboratory research applications. Often, the animals are constantly moving around, making it difficult to examine them for measurements of physiological parameters. Because of the constant movement, for example, one cannot easily attach electrodes for measuring cardiac or muscle activity to the main body section of the animal. The electrodes placed on the chest area of a small animal can also hinder movement. In addition, the large and cumbersome electrodes may cause added stress to the mammal, and may further hinder their movement.

One physiological measurement that is often useful in research applications is the electrocardiogram (ECG). The ECG is of interest to pharmacologists interested in the effects of drugs on heart rate and ECG indices. However, to date there has been some difficulty in obtaining accurate ECG readings from animals without stressing the animal, or implanting devices within the animal using a surgical procedure. The stress on the animal must be approximated to compensate for different ECG results of the stressed versus unstressed animal. Such approximations decrease the accuracy of the ECG readings. In addition, the requirement of a surgical implant can be both too time consuming and too expensive to implement when dealing with larger volumes of animals. Further, there has been some difficulty in obtaining ECG readings while the animal is moving (such as on a treadmill or in a cage).

A recent advance in the field of monitoring the ECG of small rodents non-invasively involves obtaining the required electrical signals through conductive electrodes upon which the small rodents stand. The electrical signals are obtained from the feet of the small rodent. When a small rodent is at rest, it is possible to record continuous signals. However, when the small rodent moves, the contact between the feet and the electrodes is interrupted and the ECG signal is lost. By splicing the signals as contact is re-established between the feet and the electrodes, the ECG signal is restored. However, if the small rodent is running, the stride frequency can exceed 8 Hz, such that the contact time between the foot and the electrode is less than 200 ms. The heart frequency in small rodents (e.g., a mouse) can be below 8 Hz. Thus, the interval between heart beats approaches 200 ms. Therefore, detecting ECGs through the feet of small rodents as they walk or run can be difficult.

SUMMARY OF THE INVENTION

There is a need in the art for a system and method enabling the non-invasive acquisition of physiological parameters of a mammal, while allowing the mammal to move around a predetermined area. The present invention is directed toward further solutions to address this need.

In accordance with one example embodiment of the present invention, a monitoring device for non-invasively acquiring physiological measurements of a mammal is provided. The device includes a first electrode configured to attach to an ear of the mammal in a manner suitable for obtaining a first electrical signal. A second electrode is configured to make electrical contact with a first alternate location of the mammal in a manner suitable for obtaining a second electrical signal. A third electrode is configured to make electrical contact with a second alternate location of the mammal in a manner suitable for obtaining a third electrical signal. The first electrode, second electrode, and third electrode are in communication with a signal receiver.

In accordance with an example embodiment of the present invention, the physiological measurements are measurements for creating an electrocardiogram. The mammal can be, for example, a rodent. In addition, the mammal can be conscious, to the point of moving around, while the physiological measurements are obtained.

In accordance with an example embodiment of the present invention, the receiver can include a conditioner, a recorder, a signal amplifier, and/or a processor. Further, the first alternate location can be a second ear, a foot, an arm, and/or a tail.

In accordance with an example embodiment of the present invention, the first electrode, second electrode, and third electrode each can include an electrical contact for detecting the first electrical signal in the form of at least one of a sponge, a paper material, an electrically conductive fluid reservoir, and an electrode contact means.

In accordance with an example embodiment of the present invention, an apparatus is provided for rectifying the first electrical signal, the second electrical signal, and the third electrical signal to form a cardiac electrocardiogram.

In accordance with an example embodiment of the present invention, the mammal can move about a predetermined area while in electronic communication with the first electrode, the second electrode, and the third electrode, and while readings are taken to obtain the physiological measurements.

In accordance with another example embodiment of the present invention, a device for non-invasively obtaining physiological measurements of a mammal is provided. The device includes a first electrode configured to attach to an ear of the mammal in a manner suitable for obtaining a first electrical signal. A second electrode is configured to make electrical contact with a first alternate location of the mammal in a manner suitable for obtaining a second electrical signal. A means for electrical signal detection is provided in a manner suitable for obtaining a third electrical signal. The first electrode, the second electrode, and the means for electrical signal detection are in communication with a signal receiver.

In accordance with an example embodiment of the present invention, the means for electrical signal detection is in the form of an electrically conductive fluid in which the mammal is at least partially immersed.

In accordance with another example embodiment of the present invention, a method of non-invasively obtaining a physiological measurement of a mammal is provided. The method includes connecting a first electrode to a first ear of the mammal in a manner suitable for obtaining a first electrical signal. A second electrode is electrically connected to a first alternate location of the mammal in a manner suitable for obtaining a second electrical signal. A means for electrical signal detection is electrically connected to the mammal in a manner suitable for obtaining a third electrical signal. The first electrical signal, the second electrical signal, and the third electrical signal are received at a receiver. The first electrical signal, the second electrical signal, and the third electrical signal are then rectified into the physiological measurement.

In accordance with another example embodiment of the present invention, a method of non-invasively obtaining a physiological measurement of a mammal is provided. The method includes receiving a first electrical signal originating from a first ear of the mammal. A second electrical signal originating from a first alternate location of the mammal is received. A third electrical signal originating from a second alternate location of the mammal is received. The first electrical signal, the second electrical signal, and the third electrical signal are rectified into the physiological measurement.

BRIEF DESCRIPTION OF THE DRAWINGS

The present invention will become better understood with reference to the following description and accompanying drawings, wherein.

DETAILED DESCRIPTION

Figure 1A:
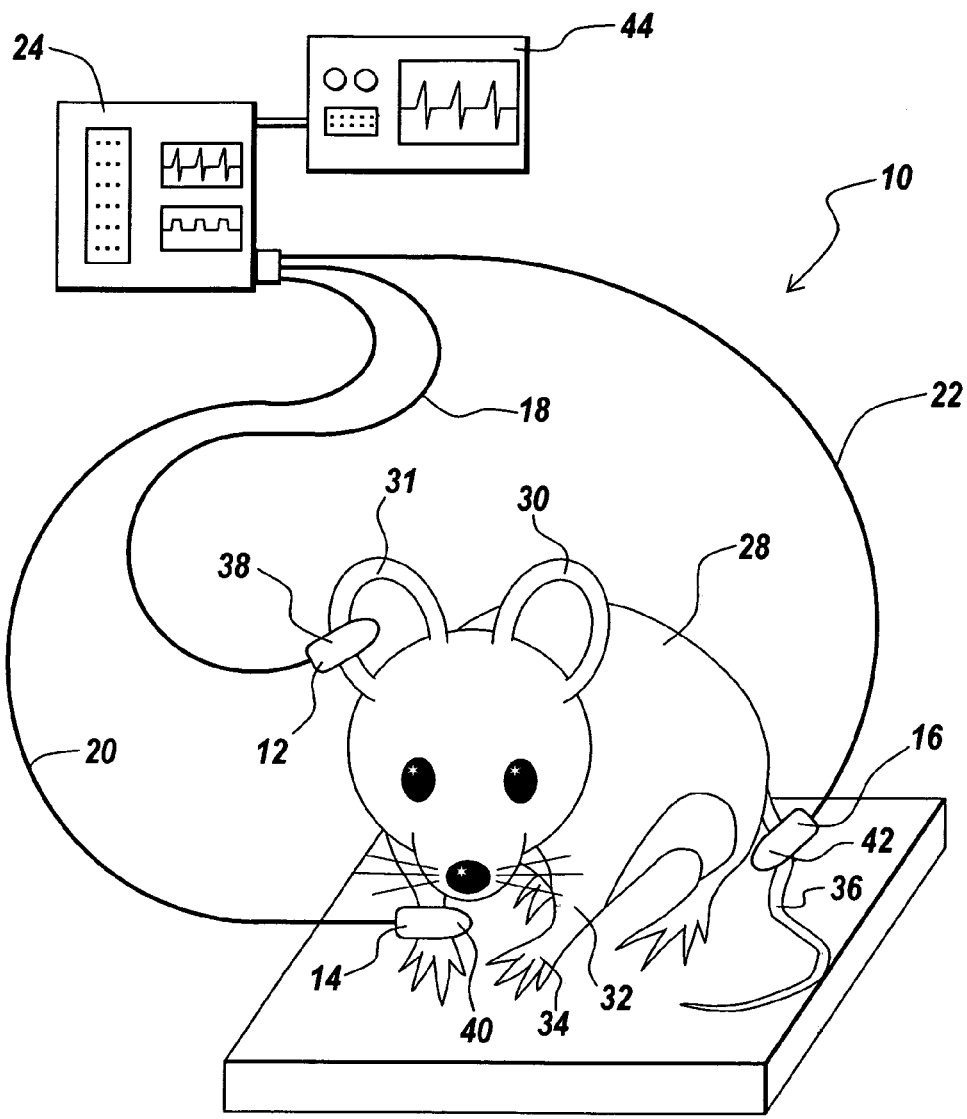
FIG. 1A is a diagrammatic illustration of a monitoring device, according to one aspect of the present invention.
Figure 1B:
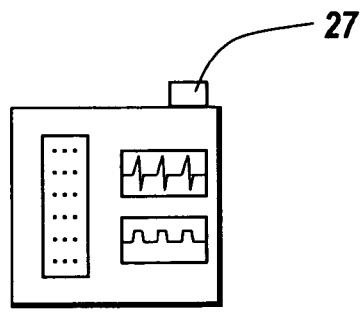
FIG. 1B is a diagrammatic illustration of a wireless version of the monitoring device of FIG. 1A.
Figure 1B:
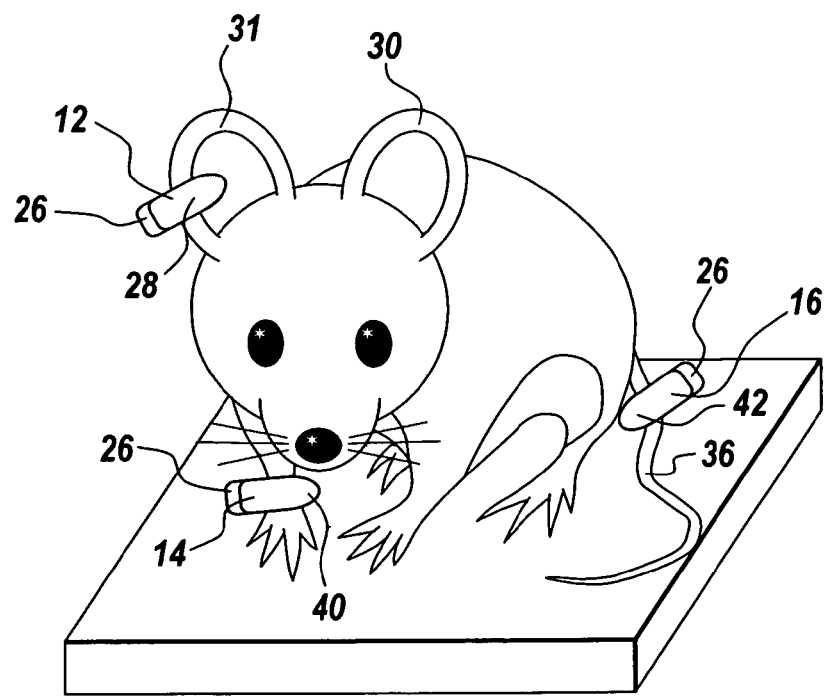

An illustrative embodiment of the present invention relates to a system and method for non-invasively acquiring one or more physiological parameter measurements from a mammal. The measurements are obtained by receiving three different electrical signals, one of which originates with at least one ear of the mammal. The mammal can be conscious, or unconscious, and can maintain the ability to move around a predetermined area or location. For example, the mammal can run on a treadmill or wander around a cage while the system and method of the present invention can actively measure the desired physiological parameters. The device reduces the level of stress experienced by the mammal relative to other devices, and avoids the need for implantation of devices in the mammal, or cumbersome external measuring devices that interfere with the mammal's movement.

FIGS. 1A through 5, wherein like parts are designated by like reference numerals throughout, illustrate example embodiments of a monitoring device for non-invasively obtaining electrical signals from a mammal according to the present invention. Although the present invention will be described with reference to the example embodiments illustrated in the figures, it should be understood that many alternative forms can embody the present invention. One of ordinary skill in the art will additionally appreciate different ways to alter the parameters of the embodiments disclosed, such as the size, shape, or type of elements or materials, in a manner still in keeping with the spirit and scope of the present invention.

FIG. 1A illustrates one example embodiment of a monitoring device 10 for obtaining physiological parameters of a mammal 28. The device 10 includes a first electrode 12 in electrical communication with a receiver 24 through a wire 18. A second electrode 14 is also in electrical communication with the receiver 24 through a wire 20. Further, a third electrode 16 is in electrical communication with the receiver 24 through a wire 22. Alternatively, one or more of the first electrode 12, the second electrode 14, and the third electrode 16 can be in electrical communication with the receiver 24 through a wireless transmitter 26. In a further alternative, the third electrode 16 can be replaced with an electrically conductive fluid reservoir, as will be discussed in greater detail later herein.

The receiver 24 receives electrical signals from each of the first electrode 12, the second electrode 14, and the third electrode 16, and can include a number of different components or features. For example, the receiver 24 can include a signal conditioner to condition the electrical signals received. The receiver 24 can include an amplifier to boost the amplitude of the signals received prior to processing. The receiver 24 can include a recorder for recording the signals received. The receiver 24 can also include a processor for controlling the receipt and manipulation of the signals received. The processor can also execute various algorithms to analyze and report the signals received.

The monitoring device 10 measures physiological parameters of a mammal 28. For purposes of illustration, the physiological parameters will be described in the form of an electrocardiogram. However, one of ordinary skill in the art will appreciate that other physiological parameters can be measured or obtained using the teachings of the present invention. Example physiological parameters include head turning via ear sensor, tail motion via tail sensor, and other physiological occurrences.

The mammal 28 is depicted herein as a mouse for illustrative purposes only. One of ordinary skill in the art will appreciate that the mammal 28 can take many forms, such as many types of rodents and other mammals that have ear structures upon which an electrode can be attached or mounted.

The first electrode 12 and a first electrical contact 38 attaches, contacts, mounts, or otherwise makes electrical contact with an ear (e.g., a left ear 30 or a right ear 31) of the mammal 28 in a manner sufficient to detect an electrical signal. The first electrode 12 includes the first electrical contact 38 to facilitate the electrical connection.

The second electrode 14 and a second electrical contact 40 attaches, contacts, mounts, or otherwise makes electrical contact with a first alternate location on the mammal 28 in a manner sufficient to detect an electrical signal. The first alternate location can be a number of different locations on the body of the mammal 28. For example, the first alternate location can be the other of the left ear 30 or the right ear 31, an arm or leg 32, a hand or foot 34, or a tail 36.

The third electrode 16 and a third electrical contact 42 attaches, contacts, mounts, or otherwise makes electrical contact with a second alternate location on the mammal 28 in a manner sufficient to detect an electrical signal. The second alternate location can also be a number different locations on the body of the mammal, such as the other of the left ear 30 or the right ear 31, the arm or leg 32, the hand or foot 34, or the tail 36.

In any one application of the monitoring device 10, the first electrode 12 and first electrical contact 38, the second electrode 14 and second electrical contact 40, and the third electrode 16 and third electrical contact 42 must all be positioned to obtain electrical signals from different locations on the body of the mammal 28. For example, the monitoring device will not work reliably if the first electrode 12 and first electrical contact 38 and the second electrode 14 and second electrical contact 40 are both in electrical communication with the same ear of the mammal 28. There must be some physical separation of body locations for the monitoring device 10 to effectively detect the electrocardiogram. Therefore, the first electrode 12 and first electrical contact 38 can make electrical contact with the left ear 30, while the second electrode 14 and second electrical contact 40 can make electrical contact with the right ear 31, and the third electrode 16 and third electrical contact can make electrical contact with the tail 36, or arm 32, or foot 34, or the like. Each of the first electrode 12, second electrode 14, and third electrode 16 can mount to the mammal 28 using a number of different methods, including a clip, mild adhesive, or being wrapped with tape, or the like. The method of mounting, or otherwise establishing electrical communication, can vary as understood by one of ordinary skill in the art, as long as sufficient electrical contact is achieved to receive the electrical signals.

Each of the first electrode 12, the second electrode 14, and the third electrode 16, communicates with the receiver 24 using respective wires 18, 20, and 22, as illustrated in FIG. 1A. Alternatively, the first electrode 12, the second electrode 14, and the third electrode 16 can communicate with the receiver 24 using a wireless transmission device 26 of FIG. 1B, if desired. The wireless transmission device 26 can communicate with a wireless receiver 27 in communication with the receiver 24. The wireless transmission can occur using, for example, an RF transmitter and receiver combination.

The first electrical contact 38, second electrical contact 40, and third electrical contact 42 can take the form of, for example, a sponge, a paper surface, a fluid reservoir with electrically conductive fluid, and/or any other suitable electrode contact means as understood by one of ordinary skill in the art. The first electrical contact 38, the second electrical contact 40, and the third electrical contact 42 can also make use of a fluid, such as water or other electrically conductive fluid. The fluid moistens the electrical contact 38, 40, or 42 and improves the electrical connectivity between the electrode 12, 14, and 16 and the mammal 28.

Figure 1C:
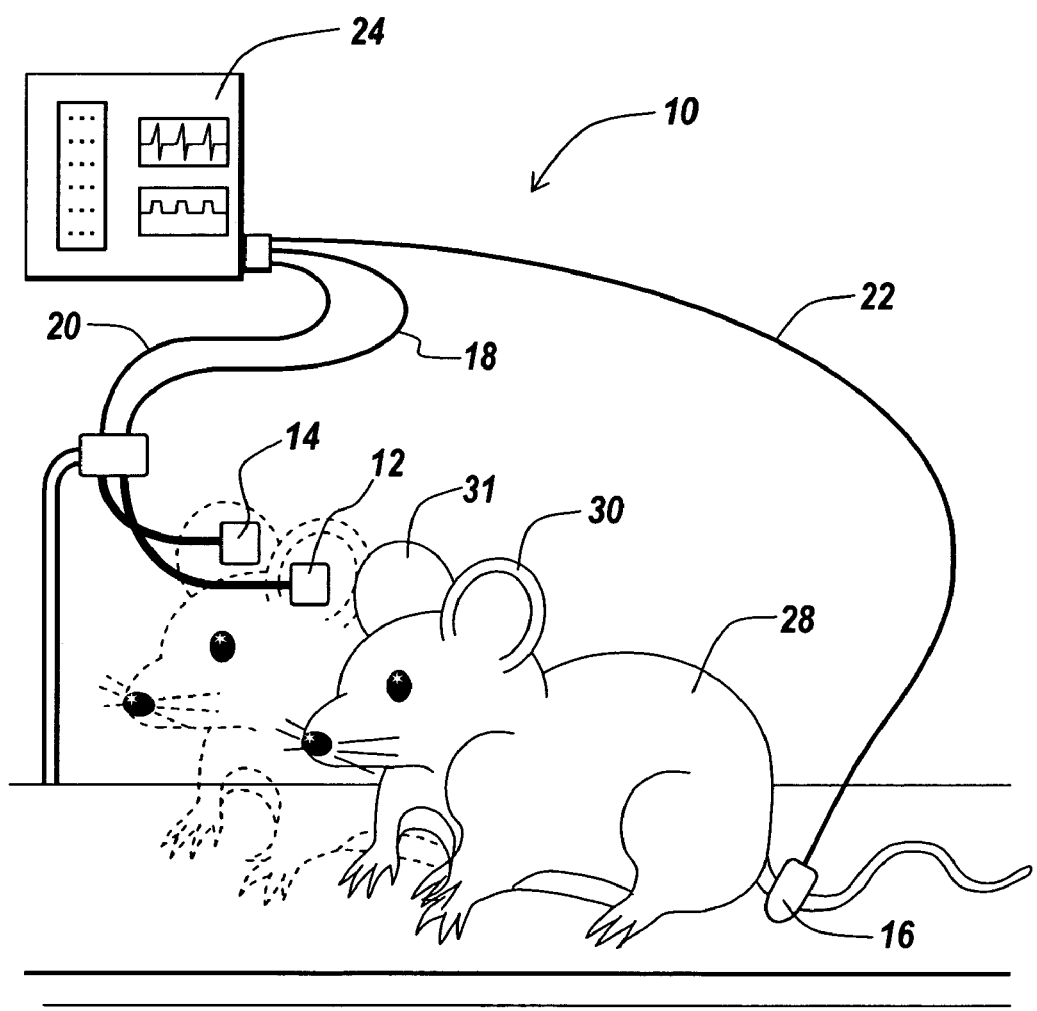
FIG. 1C is a diagrammatic illustration of a passive contact version of the monitoring device of FIG. 1A.

In still another alternative embodiment, for example, one or more of the electrodes 12, 14, and 16 can be positioned in such proximity and in the path of the mammal 28 that they passively engage and establish contact with the ears. As the mammal 28 moves, the mammal 28 passes the electrodes 12, 14, or 16 and one or both of the mammals ears 30 and 31 brush past and make contact with one or more of the electrodes 12 or 14, as depicted in FIG. 1C. Such an arrangement requires strict guidance of the path of the mammal 28, so that the ears 30 and 31 make the appropriate contact with the electrodes 12 and 14.

Figure 2:
FIG. 2 is an electrocardiogram, according to one aspect of the present invention.

The monitoring device 10 can also include a rectifier 44. The rectifier 44 connects with the receiver 24, and takes the electrical signals from the receiver to convert them into the desired physiological parameter. For example, the receiver 24 can forward the electrical signals to the rectifier 44 to create an electrocardiogram (ECG) 46 as illustrated in FIG. 2.

The ECG 46 is a representation of the electrical activity of the heart of the mammal 28. The impulses caused by the heart muscle flexing result in the creation of, for example, a P-wave, Q-wave, R-wave, T-wave, and S-wave. These waves are illustrated with corresponding letters in FIG. 2. One can utilize the different waves of the ECG to evaluate symptoms associated with heart disease, such as irregular heartbeats. The ECG can also be utilized to evaluate the health of the mammal's heart in a mammal diagnosed with a risk for heart disease, such as a mammal with high blood pressure and cholesterol levels, diabetes, or a mammal that is significantly overweight. In addition, the ECG can be utilized to monitor known heart disease, damage or abnormalities, to monitor the effects of certain medications on the heart, to monitor the function of artificial pacemakers, or to obtain information about the size of the heart.

The monitoring device 10 can be utilized in a number of different venues because it does not substantially hinder the movement of the mammal 28. For example, the monitoring device 10 can obtain readings from a mammal 28 that is in a stationary location, such as on a platform, as illustrated in FIG. 1. Alternatively, the mammal 28 can have the freedom to roam around the inside of a cage or walk on a treadmill or exercise wheel.

Figure 3:
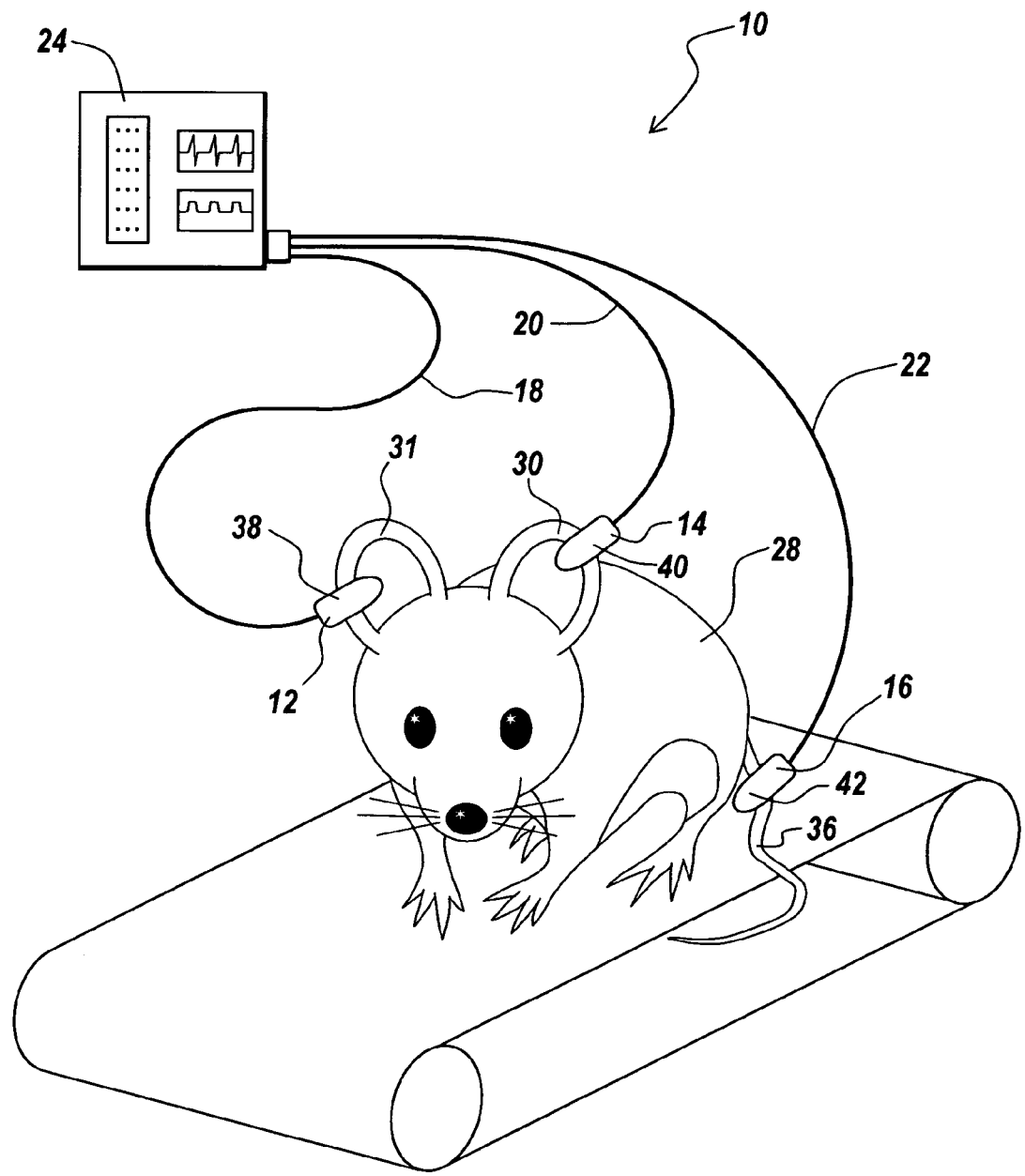
FIG. 3 is a diagrammatic illustration of the monitoring device in use with a treadmill, according to one aspect of the present invention.

In some instances, it is desirable to obtain ECG readings from the mammal 28 as it is exercising, or is otherwise being physically active. FIG. 3 illustrates the monitoring device 10 obtaining readings from the mammal 28 as the mammal 28 runs on a treadmill 48. The mammal 28 is able to run without hindrance on the treadmill because the first electrode 12 is disposed out of the way on the left ear 30 of the mammal 28, and the second electrode 14 is disposed out of the way on the right ear 31 of the mammal 28. This enables placement of the third electrode 16 in other locations on the mammal 28 identified as having little to no impact on the specific type of anticipated movement of the mammal 28. One of ordinary skill in the art will appreciate that the treadmill 48 is merely a representation of a number of different devices utilized to exercise a mammal 28, such as exercise wheels, mazes, swimming reservoir, rotating drums, elevated pegs, and the like. Such other different devices are likewise intended to fall within the scope of the present invention.

Figure 4:
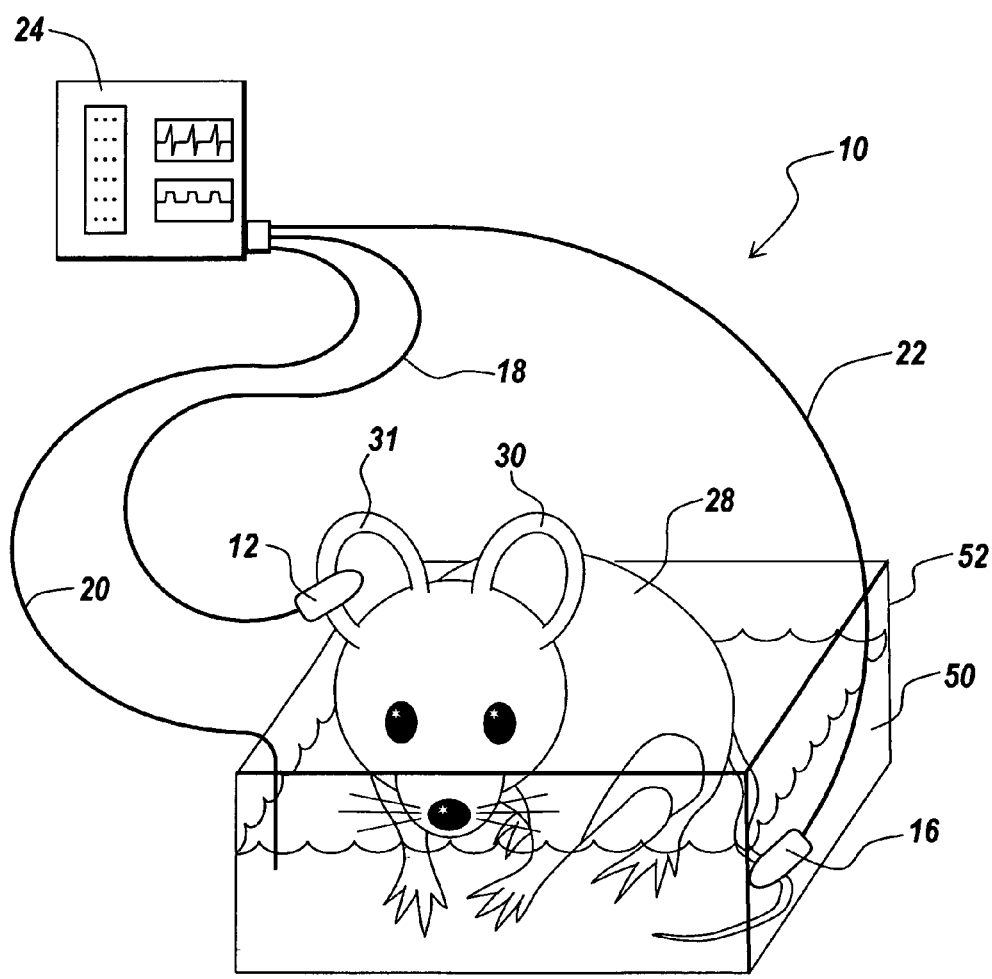
FIG. 4 is a diagrammatic illustration of an alternate embodiment of the monitoring device, according to one aspect of the present invention.

The teachings of the present invention also enable the use of alternative methods for obtaining one or more electric signals in conjunction with the signal obtained through the left ear 30 or right ear 31 of the mammal 28. For example, FIG. 4 illustrates the mammal 28 being partially submerged in an electrically conductive fluid 50 contained within a tank 52. The electrically conductive fluid 50, for example water, can act as the third electrode for receiving electrical signals. The mammal 28 can swim within the electrically conductive fluid 50, or stand on a platform or bottom surface of the tank 52, depending on the depth of the electrically conductive fluid 50. The first electrode 12 sends the first electrical signal to the receiver 24 through the first wire 18. The second electrode 14 has been replaced with the electrically conductive fluid 50, which conveys the second electrical signal through the second wire 20 to the receiver 24. The third electrode 16 sends the third electrical signal to the receiver 24 through the third wire 22.

Figure 5:
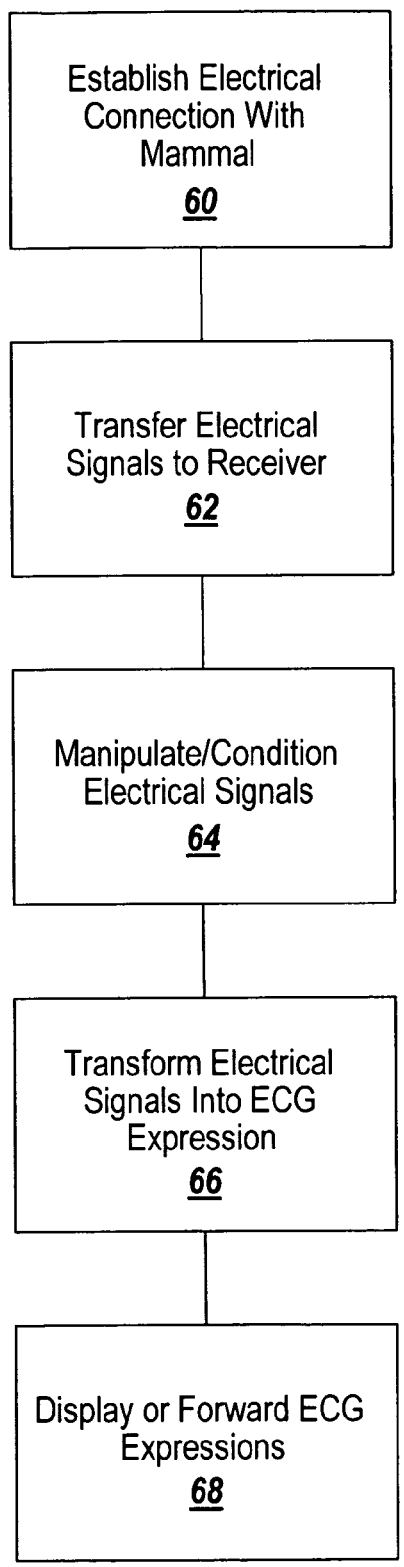
FIG. 5 is a flow chart illustrating one embodiment of a method of using the monitoring device, according to one aspect of the present invention.

In operation, the monitoring device 10 can efficiently and non-invasively acquire physiological parameter measurements from the mammal 28 without substantially hindering the movement of the mammal 28. FIG. 5 shows one example embodiment of the method executed in accordance with the teachings of the present invention. An electrical connection is made between the mammal 28 and the monitoring device 10 (step 60). The electrical connection can be in the form of establishing electrical communication between the first electrode 12 and the left ear 30 or right ear 31 of the mammal, and the second electrode 14 and the third electrode 16 with different of the other available parts of the mammal 28 (e.g., the other of the left ear 30 or right ear 31, the arm or leg 32, the hand or foot 34, or the tail 36, or with fluid 50 immersion). The electrical signals received by the electrodes 12, 14, and 16 are transferred to the receiver 24 (step 62). The receiver 24 manipulates the electrical signals to condition them for translation into a desired display (step 64). The signals are forwarded to the rectifier 44 (step 64) and transformed into ECG expressions (step 66). The ECG expressions can be displayed or forwarded to another location for interpretation, if desired (step 68).

The monitoring device 10 of the present invention enables the acquisition of physiological parameter measurements from a mammal without undue hindrance of mammal movement. The monitoring device electrically connects at least one electrode with an ear of the mammal, while the second and third electrical signals are obtained from electrodes at other locations, or by immersion of the mammal in an electrically conductive fluid. The electrical signals are obtained without use of invasive components, and the mammal is minimally to negligibly stressed by the electrodes. Therefore, there is a substantially reduced requirement of adjustment to, e.g., ECG, readings acquired from the mammal with the monitoring device 10 for environmental factors relating to the monitoring equipment. The monitoring device of the present invention, therefore, offers a fast and efficient method of obtaining such readings as ECG's from mammals, without invasive or expensive device preparation, and results in a more accurate ECG reading due to the minimal stress caused to the mammal by the monitoring device.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. It is intended that the present invention be limited only to the extent required by the appended claims and the applicable rules of law.

What is claimed is:

1. A method of non-invasively acquiring a physiological measurement of a mammal, comprising:
    establishing an electrical connection between a first electrode and a first ear of the mammal in a manner suitable for obtaining a first electrical signal;
    establishing an electrical connection between a second electrode and a first alternate location of the mammal in a manner suitable for obtaining a second electrical signal;
    establishing an electrical connection between a means for electrical signal detection and the mammal in a manner suitable for obtaining a third electrical signal;
    receiving the first electrical signal, the second electrical signal, and the third electrical signal at a receiver; and
    rectifying the first electrical signal, the second electrical signal, and the third electrical signal into the physiological measurement;
    wherein the physiological measurement comprises an electrocardiogram.

2. The method of claim 1, wherein the mammal comprises a rodent.

3. The method of claim 1, wherein establishing an electrical connection comprises positioning the first electrode and the second electrode with at least one of a removable fastener and/or structure supporting at least one of the first electrode and/or the second electrode for passive contact with the mammal.

4. A method of non-invasively acquiring a physiological measurement of a mammal, comprising:
    receiving a first electrical signal originating from a first ear of the mammal;
    receiving a second electrical signal originating from a first alternate location of the mammal;
    receiving a third electrical signal originating from a second alternate location of the mammal; and
    rectifying the first electrical signal, the second electrical signal, and the third electrical signal into the physiological measurement;
    wherein the physiological measurement comprises an electrocardiogram.

5. The method of claim 4, wherein the mammal comprises a rodent.

6. The method of claim 1, wherein the mammal is conscious while the physiological measurements are obtained.

* * * * *